United States Patent
Maclaren et al.

(10) Patent No.: US 10,993,621 B2
(45) Date of Patent: May 4, 2021

(54) CONTACT-FREE PHYSIOLOGICAL MONITORING DURING SIMULTANEOUS MAGNETIC RESONANCE IMAGING

(71) Applicant: The Board of Trustees of the Leland Stanford Junior University, Palo Alto, CA (US)

(72) Inventors: Julian Maclaren, Menlo Park, CA (US); Murat Aksoy, Menlo Park, CA (US); Roland Bammer, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/114,021

(22) PCT Filed: Feb. 2, 2015

(86) PCT No.: PCT/US2015/014110
§ 371 (c)(1),
(2) Date: Jul. 25, 2016

(87) PCT Pub. No.: WO2015/117084
PCT Pub. Date: Aug. 6, 2015

(65) Prior Publication Data
US 2016/0331239 A1 Nov. 17, 2016

Related U.S. Application Data

(60) Provisional application No. 61/935,222, filed on Feb. 3, 2014.

(51) Int. Cl.
*A61B 5/02* (2006.01)
*A61B 5/00* (2006.01)
(Continued)

(52) U.S. Cl.
CPC .............. *A61B 5/0077* (2013.01); *A61B 5/02* (2013.01); *A61B 5/055* (2013.01); *A61B 5/08* (2013.01);
(Continued)

(58) Field of Classification Search
CPC ... A61B 5/0077; A61B 5/0082; A61B 5/0873; A61B 5/1128; A61B 5/113
See application file for complete search history.

(56) References Cited

U.S. PATENT DOCUMENTS

| 4,945,916 A | 8/1990 | Kretschmer |
| 6,185,446 B1 | 2/2001 | Carlsen, Jr. |

(Continued)

FOREIGN PATENT DOCUMENTS

WO WO2013074578 5/2013

OTHER PUBLICATIONS

Bartula et al. "Camera-based System for Contactless Monitoring of Respiration," 35th Annual International Conference of the IEEE, Osaka, Japan, pp. 2672-2675, Jul. 2013. (Year: 2013).*

(Continued)

*Primary Examiner* — Eric D. Bertram
(74) *Attorney, Agent, or Firm* — Lumen Patent Firm (57) ABSTRACT

Devices and methods to measure and visualize the cardiac and respiratory signal of a human or animal subject during a magnetic resonance imaging (MRI) exam are described. This includes a video camera compatible with the MRI scanner, a means of transferring the video data away from the MRI scanner, a light source that illuminates the subject, and an algorithm that analyses the video stream and uses small image intensity changes and motion information to extract cardiac signal and respiratory signals of the subject. These methods make it practical to use optical tracking to monitor and correct for cardiac and respiratory motion (Continued)

during MRI, as well as provide basic patient monitoring with no physical contact to the subject.

12 Claims, 6 Drawing Sheets

(51) Int. Cl.
    *A61B 5/055*     (2006.01)
    *A61B 5/113*     (2006.01)
    *G01R 33/28*     (2006.01)
    *G01R 33/567*     (2006.01)
    *A61B 5/11*     (2006.01)
    *A61B 5/08*     (2006.01)

(52) U.S. Cl.
    CPC ............ *A61B 5/1102* (2013.01); *A61B 5/113* (2013.01); *A61B 5/1128* (2013.01); *A61B 5/7225* (2013.01); *A61B 5/7257* (2013.01); *A61B 5/7278* (2013.01); *G01R 33/283* (2013.01); *G01R 33/5673* (2013.01)

(56) References Cited

U.S. PATENT DOCUMENTS

| | | | |
|---|---|---|---|
| 6,816,266 B2 | 11/2004 | Varshneya | |
| 7,988,688 B2 | 8/2011 | Webb | |
| 8,121,361 B2 | 2/2012 | Ernst | |
| 8,214,012 B2 | 7/2012 | Zuccolotto | |
| 8,805,019 B2 | 8/2014 | Jeanne | |
| 2004/0236229 A1* | 11/2004 | Freeman | A61B 5/0059 600/474 |
| 2007/0238951 A1* | 10/2007 | Ferenczi | A61B 5/055 600/407 |
| 2009/0209846 A1* | 8/2009 | Bammer | A61B 5/055 600/421 |
| 2010/0245543 A1 | 9/2010 | Greer | |
| 2011/0201916 A1 | 8/2011 | Duyn | |
| 2012/0121124 A1 | 5/2012 | Bammer | |
| 2013/0030257 A1 | 1/2013 | Nakata | |
| 2013/0296660 A1* | 11/2013 | Tsien | A61B 5/0077 600/301 |
| 2014/0037174 A1* | 2/2014 | Ernst | A61B 5/1127 382/131 |
| 2014/0046167 A1 | 2/2014 | Vij | |
| 2014/0303899 A1* | 10/2014 | Fung | B60R 25/25 702/19 |

OTHER PUBLICATIONS

Verkruysse et al. Remote plethysmographic imaging using ambient light. 22 Opt Express. Dec. 22, 2008; 16(26): 21434-21445.
Maclaren et al. MRI with TRELLIS: a novel approach to motion correction. Magnetic Resonance Imaging 26 (2008) 474-483.
Maclaren et al., "Measurement and Correction of Microscopic Head Motion during Magnetic Resonance Imaging of the Brain", 2012, Plos One v7n11 e48088.

* cited by examiner

CONTACT-FREE PHYSIOLOGICAL MONITORING DURING SIMULTANEOUS MAGNETIC RESONANCE IMAGING

CROSS-REFERENCE TO RELATED APPLICATIONS

This application is a 371 of PCT/US2015/014110 filed on Feb. 2, 2015. PCT/US2015/014110 filed on Feb. 2, 2015 claims the benefit of U.S. Provisional Application 61/935,222 filed on Feb. 3, 2014.

GOVERNMENT SPONSORSHIP

This invention was made with Government support under contract EB011654 awarded by the National Institutes of Health. The Government has certain rights in the invention.

FIELD OF THE INVENTION

This invention relates to physiological monitoring in a magnetic resonance imaging system.

BACKGROUND

Magnetic resonance imaging (MRI) is a valuable imaging technique for humans and animals. MRI is often used for imaging the human body, both for research and for clinical purposes, such as for the diagnosis of numerous diseases and for surgical planning.

Magnetic resonance imaging is typically performed with the patient lying in a long narrow bore and with the body part of interest located in a confined coil, which is used to receive signal for image reconstruction. A single scan lasts on the order of minutes. The entire exam typically includes several scans and lasts on the order of tens of minutes.

Monitoring of patient cardiac and respiratory signals is necessary in many MR imaging situations. The electrocardiograph signal is often used to track the cardiac cycle. However, this requires the attachment of electrodes and the signal is often corrupted by the scanner RF field, the imaging gradients, and motion of the electrodes in the main magnetic field. An alternative is a finger-mounted pulse oximeter (photoplethysmograph), but this also requires interaction with the subject, and motion of the pulse oximeter can lead to false readings. Respiratory motion is often measured using an air-filled belt attached to a pressure sensor. This also requires a device to be attached to the subject.

There is a need for an alternative method to measure physiological signals from subjects during MRI that requires no physical contact to the subject, no extra setup time for the scanner operator and operates at all field strengths used in MRI. These field strengths span two orders of magnitude from approximately 0.1 T to 10 T, but field strengths of 1.5 T and 3 T are of particular relevance since they are often employed in clinical practice.

SUMMARY

The present invention addresses the need discussed above, i.e., the ability to obtain physiological parameters and perform physiological monitoring without contact to the human or animal subject, without interaction by the scanner operator and with no performance penalty at high field strengths.

It is well known to those skilled in the art that it is possible to operate a video camera inside an MRI scanner for the purposes of motion tracking. This is done by attaching a marker to the subject, which is then used to compute pose (position and orientation) information and track motion from frame to frame. In this work, we describe a number of adaptions that can be made to optical motion correction systems in order to obtain physiological parameters from the subject. By performing validation experiments comparing the calculated physiological parameters to those measured using traditional approaches, we show that this method is effective.

Instead of imaging a marker, one or more cameras are integrated into the MRI system, such that the camera field of view includes the forehead of the subject. In this way, no extra physical contact is made to the subject for the purpose of physiological monitoring.

In a preferred embodiment, a single camera is integrated into the head coil of the MRI scanner and directed towards the forehead of a human subject, such that the obtained video data is a video of their skin. A white light emitting diode (LED) can provide illumination of the skin, and color video data can be collected using the camera. Video data can be transmitted out of the MRI scanner room in real time via an optical link. The optical link advantageously avoids a galvanic contact to the camera, thereby providing MRI compatibility.

In a preferred embodiment, the video data stream is continuously visible to the scanner operator outside the scanner room. In addition, real-time image processing (as described below) can be employed to extract cardiac and/or respiratory information from the video stream. In the case of cardiac information, this is possible due to slight changes in reflected light that occur as blood moves through the vascular bed. In the case of respiratory information, this is possible due to slight head movements that occur as the subject inhales and exhales. This processed information can also be made available to the operator in real time via the computer normally used to operate the MRI scanner, and where cardiac and respiratory information obtained using traditional methods (pulse oximeter, ECG, respiratory belt) is normally shown.

In another embodiment, the video data visible to the scanner operator is augmented, such that cardiac pulsations of the subject are clearly visible. This can be done by modifying the color channels to enhance temporal signal changes taking place in particular regions in the image. Further information concerning this embodiment is provided below.

In another embodiment, the video data visible to the scanner operator is augmented, such that motion occurring due to respiration of the subject is enhanced and is more visible in the augmented video frames than in the original video frames.

In another embodiment, the camera sensor is replaced with a sensor that has high sensitivity to the infrared part of the electromagnetic spectrum. In this way, the video data can be used for high-temporal resolution monitoring of patient skin temperature.

DETAILED DESCRIPTION

Figure 1:
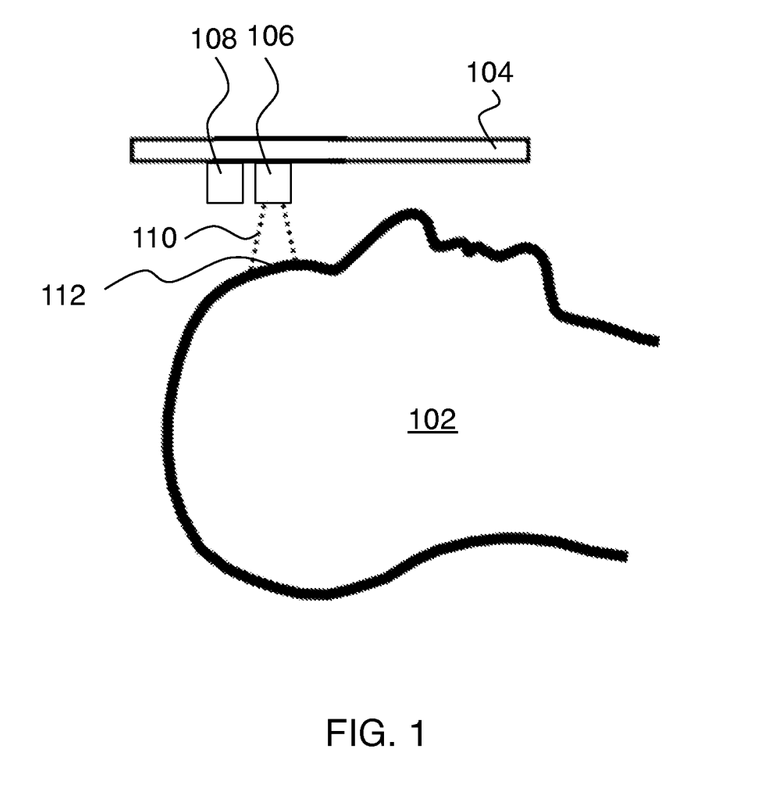
FIG. 1 shows how a video can be obtained of skin on a patient's forehead by integrating an MR-compatible camera into an MRI imaging head coil.

FIG. 1 shows an MR-compatible camera 108 embedded into a head coil 104 of the MRI system. The MRI system is equipped with an optical source 106, which provides light 110 to illuminate a patch of skin 112 on the forehead of a subject 102, who is lying on the patient table and undergoing an MRI examination. Alternatively, 106 can be a camera that includes an optical source for illumination.

Figure 2:
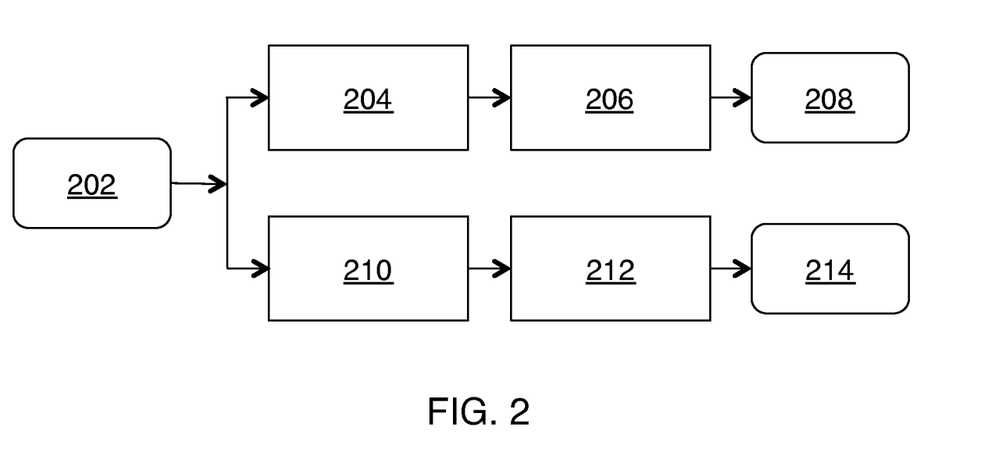
FIG. 2 is an exemplary block diagram showing how cardiac and respiratory information can be computed from video data to produce the results shown herein.

FIG. 2 shows how cardiac and respiratory information can be computed from video data to produce the results shown here. The same video stream is used to generate both cardiac and respiratory signals from the same data. In this example, the starting point 202 is video that is acquired at a rate of 30 frames/second. Sampling may be faster or slower than this; however, we have generally found 30 Hz to be sufficient for this application. To compute the cardiac signal, the mean pixel intensity 204 is taken over the entire image, or over subsections of the image, for each frame. This signal is then filtered using a bandpass filter 206 with passband between 0.6 Hz and 10 Hz to provide cardiac data 208. To compute the respiratory signal, motion of the image in the head-feet direction is calculated using 1D sub-pixel image registration 210. This provides an effective means to capture the slight 'nodding' motion that accompanies respiration. The signal is then filtered using a bandpass filter 212 with passband from 0.2 Hz to 0.6 Hz to provide respiratory data 214.

Figure 3:
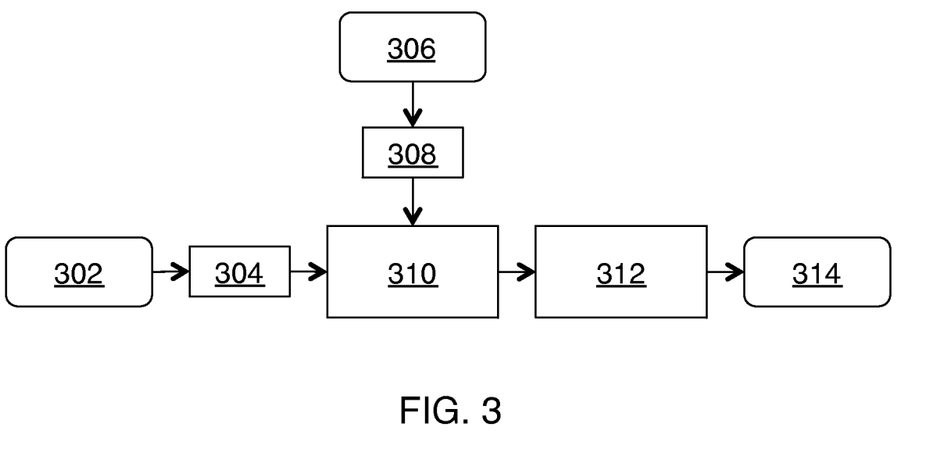
FIG. 3 is an exemplary block diagram showing further details relating to determining respiratory motion from the video data.

FIG. 3 provides further details relating to the computation of the respiratory signal. The 1D motion module 210 shown in FIG. 2 performs image registration using a sub-pixel implementation of the phase correlation method. FIG. 3 is a block diagram of this method. As in the pixel intensity module, each frame is initially cropped to a 360×360 square, removing the stationary head coil, which would otherwise be a confounding factor in the motion calculation. The first frame in the video sequence is used as a reference frame 306. Each of following frames 302 in the video are compared to this reference frame to compute the relative displacement in the image x- and y-directions. This is achieved by applying the inverse FFT to both the reference and ith cropped frames (308 and 304 respectively) and computing the phase difference in the Fourier domain 310. This phase difference is a 2D ramp with a gradient proportional to the displacement between the two frames. This gradient, and hence the displacement, is found using the sub-pixel phase correlation method 312, described in more detail by Maclaren et al. in "MRI with TRELLIS, a novel approach to motion correction" (Magnetic Resonance Imaging v26 (2008) pp. 474-483), hereby incorporated by reference in its entirety, to provide output x and y shifts 314. The shift in the image x-direction (patient left-right) is discarded and only the shift in the image y-direction (patient head-feet, also referred to as the longitudinal direction) is used for further processing.

Figure 4A:
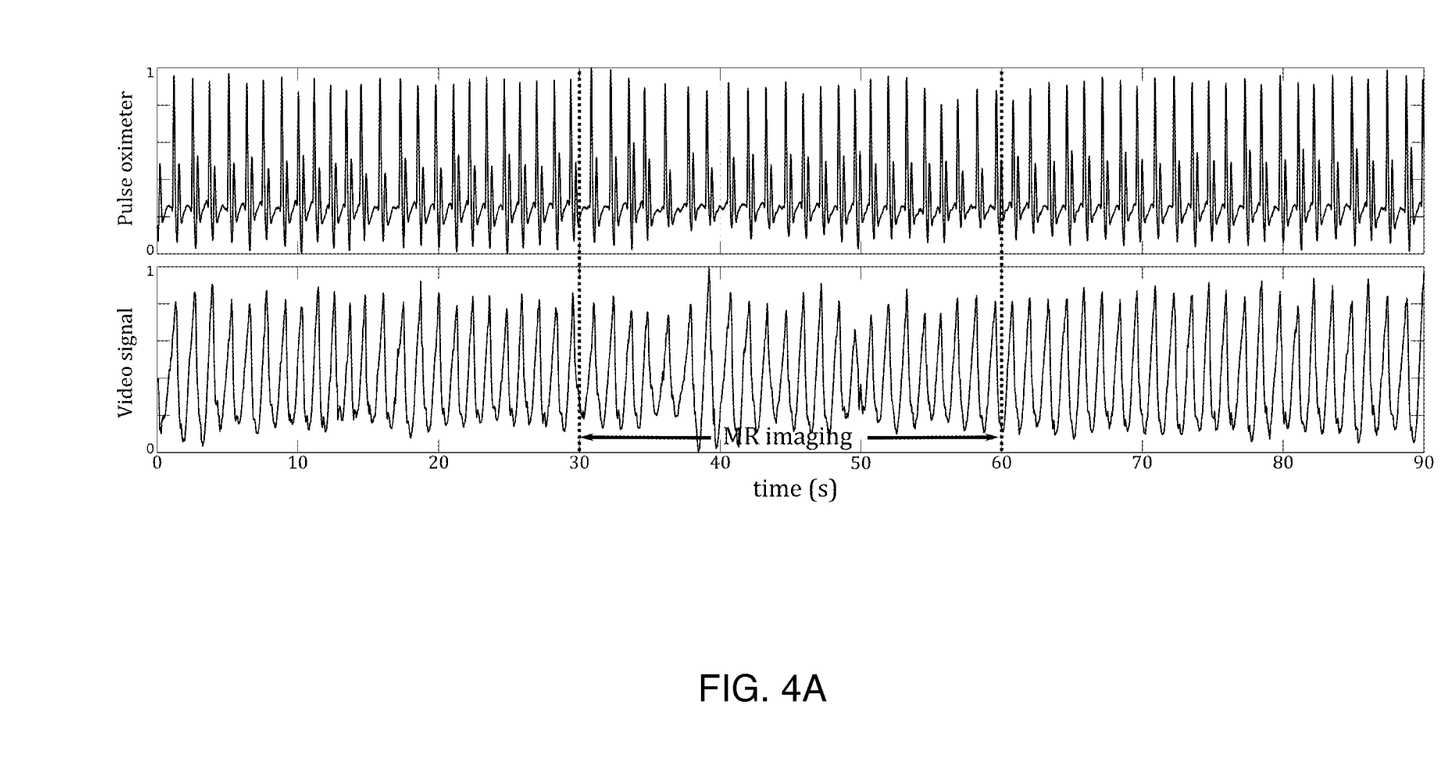
FIG. 4A shows a plot comparing the cardiac signal calculated from the video data and the signal obtained simultaneously from a subject using a pulse oximeter.

FIG. 4A shows a plot comparing the cardiac signal calculated from the video data, using the methods described here, and the signal obtained simultaneously from a subject using a pulse oximeter. In this experiment, we began imaging with the MRI scanner after 30 s and stopped imaging with the MRI scanner after 60 s. This period is marked on the graph. No change in the calculated cardiac signal over this time period is visible, indicating that scanning had no significant effect on the camera. Pulsations measured with both systems coincide, which indicates that the signal obtained from the video-processing algorithm is genuinely related to cardiac pulsation. A good match to the pulse oximeter data is apparent for the video intensity signal in terms of the timing and magnitude of peaks.

Figure 4B:
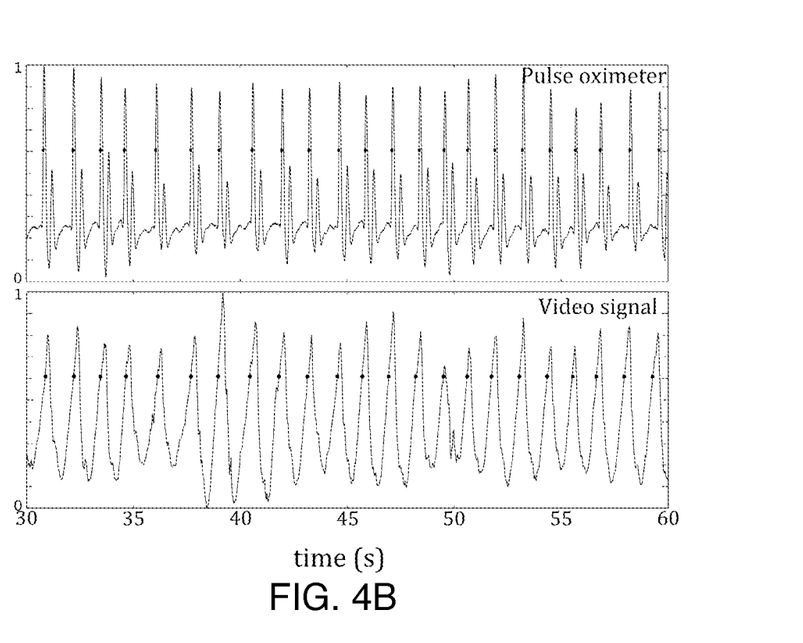
FIG. 4B shows a plot comparing the triggering provided by the cardiac signal calculated from the video data to the triggering provided by the signal obtained from the pulse oximeter.
Figure 4C:
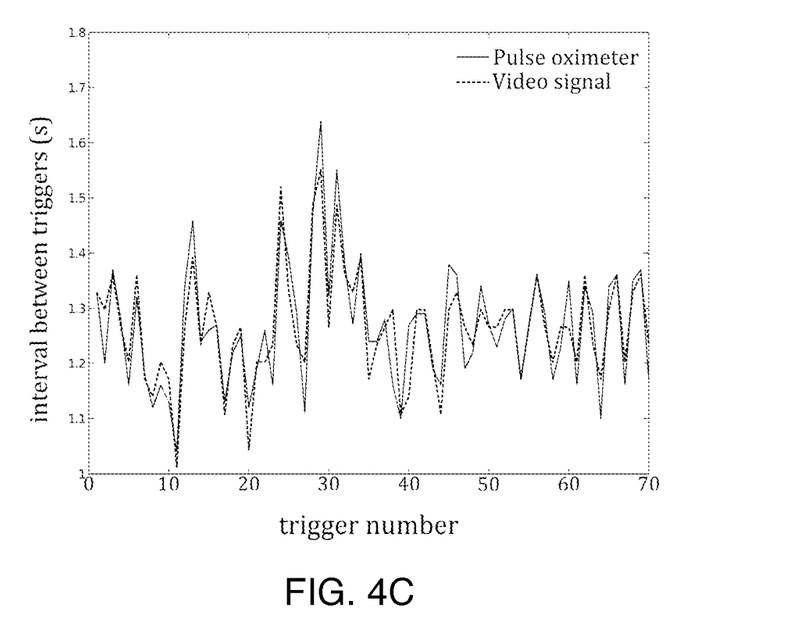
FIG. 4C is a further comparison of the triggering provided by the cardiac signal calculated from the video data to the triggering provided by the signal obtained from the pulse oximeter.

To provide a better comparison of the potential usefulness of the cardiac signals for cardiac gating, a simple algorithm was applied in order to check for consistency of the time period between detected pulses (equivalent to the RR interval in ECG). Trigger locations were found for each curve based on two parameters: a threshold, set arbitrarily to 0.6 (where the signals are normalized to have a peak value of 1), and a minimum interval time, set here to be 300 ms. Trigger locations were then defined as any time point more than 300 ms since the previous trigger, where the signal crossed the 0.6 threshold and had positive gradient. These trigger locations were then used to calculate the trigger-trigger interval time. Trigger locations, computed as described above, match well between the reference pulse oximeter data and the video intensity signal. FIG. 4B shows a zoomed-in subset of trigger locations (marked as black dots) from the central 30 s period in FIG. 4A. Although synchronization between the two signals was not perfect in our setup, there is a clear one-to-one mapping between triggers derived from the two signals. That is, every trigger detected in the pulse oximeter data stream was also detected in the video intensity signal and there were no extra triggers detected in the video intensity signal that were not detected in the pulse oximeter signal. This one-to-one mapping makes it possible to compare the time interval between triggers, as shown on FIG. 4C. The changing time interval is highly correlated: the difference between trigger intervals from the pulse oximeter and the video intensity signal has a mean of <0.01 s and standard deviation of 0.05 s, meaning that most trigger intervals computed from the two signals are within 50 ms of each other.

Figure 5:
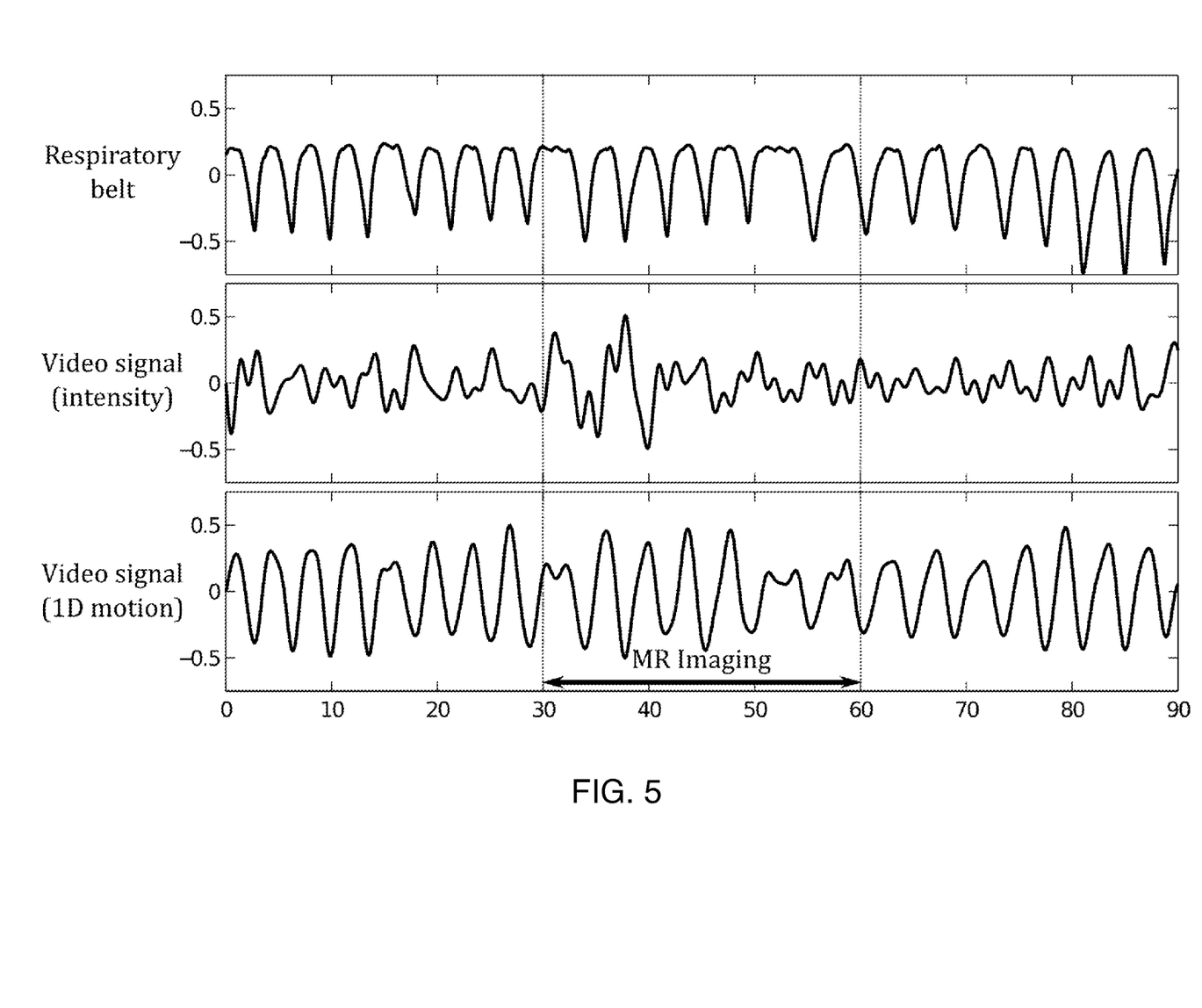
FIG. 5 shows a plot comparing the respiratory signal calculated from the video motion data to the signal obtained simultaneously from a subject using the respiratory belt and to the video intensity data.

FIG. 5 compares respiratory data from the respiratory belt to the video-derived intensity and motion signals. In this case, there is no evidence that the intensity based signal correlates with the signal from the respiratory belt. However, motion based data correlates strongly. In some cases the respiratory belt signal appears to have saturated, but the video motion signal does not, perhaps indicating further motion past the maximum range of the respiratory belt. Again, MR imaging appears to have no effect on the acquired physiological data. In summary, the signal from the respiratory belt coincides well with the results computed from the video motion signal, indicating that the computed signal is indeed due to respiration of the subject.

Figure 6:
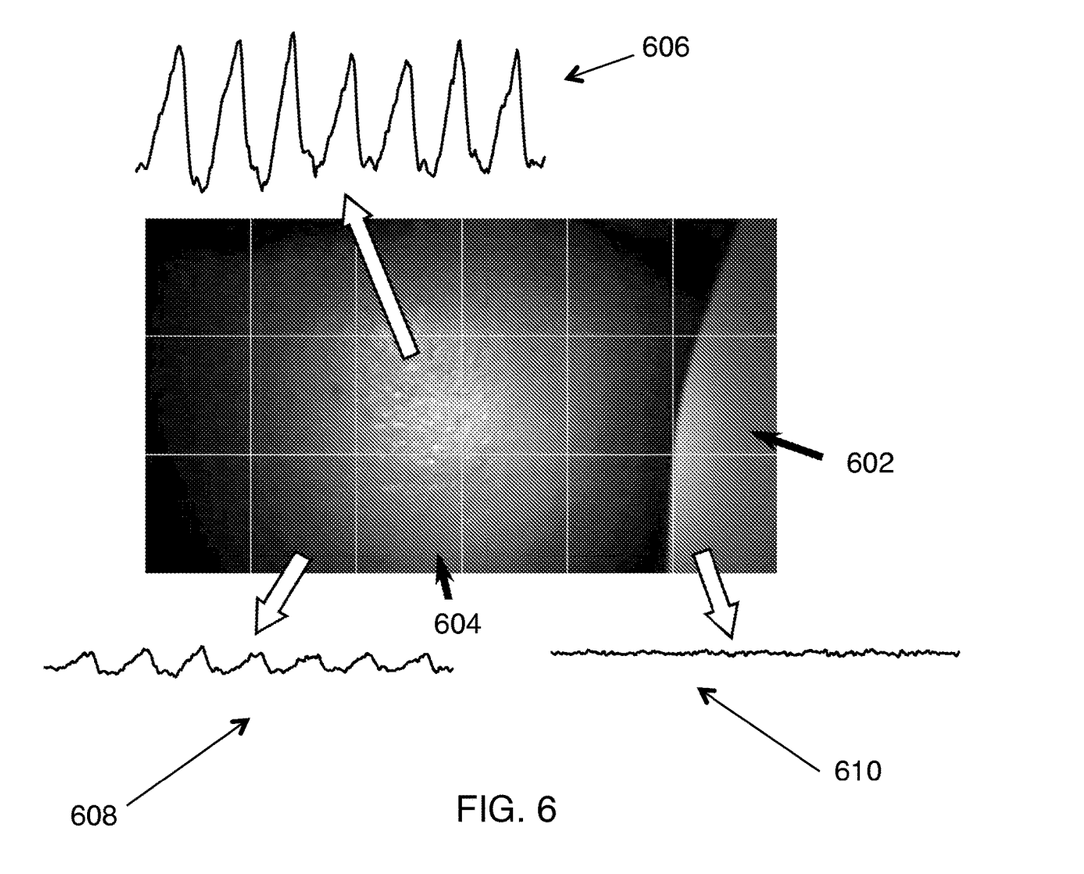
FIG. 6 shows variations in cardiac signal from different image regions.

FIG. 6 shows how different parts of the image can have substantially different video intensity signals. For example, the MRI head coil 602 provides no cardiac signal 610, while parts of the image showing the skin of the patient 604 can provide a strong signal 606 or a weak signal 608 depending on details of the configuration. For some regions the cardiac signal is particularly strong; for others (such as regions containing little skin), it is virtually non-existent. This spatial information can be fed back and used to enhance the image with a colored overlay.

Previous work, unrelated to MRI, has shown that it is possible to augment video data to make subtle intensity changes visible to the naked eye. Using a similar method, we augmented the video data acquired for this work using the video-derived cardiac signal and the following algorithm. Rather than cropping the video frames to a square and processing all pixels in that square together, frames are divided into an m-by-n grid. Processing is applied to all pixels in each grid square separately to extract the video-derived cardiac signal for each m, n. This m-by-n signal is then resampled using bicubic interpolation to the original video resolution and used to generate a 'modulation video'. The modulation video is superimposed onto the red channel of the otherwise grayscale images. Cardiac pulsation can then be easily seen as a red tone overlaid on the original video. Depending on the values selected for m and n, spatial discrimination can be traded for robustness and SNR of the signal.

In summary, our data indicate that the methods taught here enable one to obtain similar information to the pulse oximeter and respiratory belt without physical contact to the subject. Finger-mounted pulse oximetry has existed since the 1930s and the use of both the pulse oximeter and respiratory belt has been common in clinical MRI since its inception. Here we show that camera hardware can be used for physiological monitoring purposes, potentially eliminating the need to use devices that physically contact the patient.

We have not thoroughly quantified the algorithm's robustness to large-scale head motion. In the data shown, the maximum image displacement from the initial position was 16 pixels (approximately 3 mm), indicating that the subject did not remain perfectly still during the experiment. Some motion robustness can therefore be assumed. However, multiple cameras could perhaps be used in order to ensure that a sufficiently large region of skin remains in the camera field of view at all times. Motion sensitivity is a challenge shared by pulse oximetry, so our method may in fact be more robust than the state of the art.

The algorithms described in this work do not require color information in the video signal. This enables the methods taught here to be applicable to both monochrome and color image sensors. Illumination (here a white LED) is clearly necessary, as previous attempts at photoplethysmography using ambient light have been in a well-lit environment, which is not representative of the bore of an MRI scanner.

The invention claimed is:

1. Apparatus for physiological monitoring of a patient in a magnetic resonance imaging (MRI) system, the apparatus comprising:
an MRI compatible optical camera disposed within the MRI system and configured to observe a forehead of the patient;
an MRI compatible optical source disposed within the MRI system and configured to illuminate the forehead of the patient;
a processor configured to receive a video signal from the MRI compatible optical camera and to provide an output of physiological data obtained by automatic analysis of the video signal;
wherein the physiological data includes at least respiration data derived from measurements of image motion in a head-feet direction of the patient in an optical image of skin of the patient's forehead in the video signal;
wherein the image motion in the head-feet direction is determined by Fourier image processing of frames of a video sequence of the forehead of the patient;
wherein the measurements of longitudinal image motion in the video signal include computing sub-pixel longitudinal image motion using a phase correlation method.

2. The apparatus of claim 1, wherein the physiological data further includes cardiac data derived from measurements of intensity changes in the video signal.

3. The apparatus of claim 2, wherein the measurements of intensity changes in the video signal include relative intensity measurement of two or more color channels.

4. The apparatus of claim 1, wherein the MRI compatible optical source provides visible light and wherein the MRI compatible optical camera is sensitive to the visible light.

5. The apparatus of claim 1, wherein the MRI compatible optical source provides infrared light and wherein the MRI compatible optical camera is sensitive to the infrared light.

6. The apparatus of claim 1, wherein the MRI compatible optical source includes a light emitting diode.

7. The apparatus of claim 1, wherein the processor is configured to provide a further output of an image that is enhanced to emphasize temporal changes.

8. The apparatus of claim 7, wherein the temporal changes are emphasized by color coding.

9. The apparatus of claim 7, wherein the temporal changes relate to cardiac activity.

10. The apparatus of claim 7, wherein the temporal changes relate to respiration.

11. The apparatus of claim 1, wherein the MRI system is configured to account for the physiological data during MRI scanning.

12. The apparatus of claim 1, wherein the MRI compatible optical camera and the MRI compatible optical source are configured as an integrated source-camera unit.

* * * * *